US00PP12102P2

(12) United States Plant Patent
Asdoorian et al.

(10) Patent No.: US PP12,102 P2
(45) Date of Patent: Sep. 25, 2001

(54) PEACH TREE NAMED 'ISLAND PRINCE'

(76) Inventors: Alan R. Asdoorian; Lora A. Asdoorian, both of 522 6th Ave., Kingsburg, CA (US) 93631

( * ) Notice: Subject to any disclaimer, the term of this patent is extended or adjusted under 35 U.S.C. 154(b) by 0 days.

(21) Appl. No.: 09/580,400

(22) Filed: May 26, 2000

(51) Int. Cl.[7] ..... A01H 5/00

(52) U.S. Cl. ..... Plt./197

(58) Field of Search ..... Plt./197

(56) References Cited

U.S. PATENT DOCUMENTS

| | | | |
|---|---|---|---|
| P.P. 6,025 | 9/1987 | Balakian | Plt./197 |
| P.P. 9,199 | 7/1995 | Asdoorian | Plt./197 |

*Primary Examiner*—Bruce R. Campell
*Assistant Examiner*—Susan B. McCormick
(74) *Attorney, Agent, or Firm*—Mark D. Miller

(57) ABSTRACT

A new and distinct variety of peach tree which is somewhat similar to the 'Island King' peach tree (U.S. Plant Pat. No. 9,199) from which it is a sport, but from which it is distinguished by producing a later ripening fruit which are mature approximately ten to fourteen days after the fruit produced by the 'Island King' peach tree.

1 Drawing Sheet

BACKGROUND OF THE NEW VARIETY

The present invention refers to a new variety of peach tree which will hereinafter be denominated as the 'Island Prince' peach tree which produces clingstone fruit which are mature for commercial harvesting and shipment approximately May 8–10 in a normal growing year in the San Joaquin Valley of Central California as an early fresh market peach with a good red blush coloration.

In the development of new commercial varieties of fruit specific characteristics places a premium on those varieties, which are early or late maturing, in the growing season. However, many such varieties have small size, lack of flavor, or coloration. In some instances there are other undesirable characteristics that decrease the commercial success. In order for a fruit to be a commercial success it must possess those characteristics of good size, good color, and good flavor. At the same time the date of maturity must be separate or different than other similar fruit. This new invention meets all of the aforementioned criteria and therefore is of commercial appeal to the consumer.

ORGIN AND ASEXUAL REPRODUCTION OF THE NEW VARIETY

The present variety of peach tree was discovered by the inventor in his 4-acre orchard of 'Island King' peach trees (U.S. Plant Pat. No. 9,199) which is located near Kingsburg, Calif. The inventor discovered it as a sport of the 'Island King' peach tree in 1997. The new variety was first asexually reproduced by the inventor in 1997 by bud grafting two trees on Nemaguard Rootstock in the orchard of orgin. The asexually reproduced trees first bore fruit of the new variety in May 1998. The inventor carefully compared the asexually reproduced trees with the parent sport, including the fruit thereof and the parent as well as the progeny is in all respects identical.

SUMMARY OF THE NEW VARIETY

The 'Island Prince' peach is characterized by producing an extra large clingstone fruit which has good red blush coloration and is ripe for commercial harvesting and shipment approximately May 8 to May 10 in the San Joaquin Valley of Central California. The new variety is most similar to 'Island King' peach tree (U.S. Plant Pat. No. 9,199) from which it is a sport but from which is distinguishable in that it ripens ten to fourteen days later than the fruit of 'Island King' peach tree and in that the fruit is about one-third again larger in size than that of the 'Island King' peach tree. The fruit of this new variety possesses a very good flavor as well as aroma which is greatly acceptable for an early ripening variety.

BRIEF DESCRIPTION OF THE DRAWING

The accompanying drawing is a color photograph showing fruit and foliage of the new variety. The view on the left side of the photograph displays a fruit cut in half showing the pit and the flesh on the upper half and the pit well and the flesh on the bottom half. In the center is the fruit showing the distal end and the suture, while on the upper right is a fruit showing a side view with the cheek surface. The fruit on the bottom right shows the stem end of the fruit. The top of the photograph shows the foliage typical of this variety of peach tree.

DETAILED DESCRIPTION

Referring more specifically to the pomological description of this new and distinct variety of peach tree, the following has been observed under the ecological conditions prevailing in the orchard or origin which is located near Kingsburg, Calif. in the San Joaquin Valley of Central California. All major color code designations are by reference to the Dictionary of Color by Maerz & Paul, First Edition 1930. Common color names are also occasionally employed.

TREE

Size: Tree is similar in size and growth habit to 'Island King' U.S. Plant Pat. No. 9,199 — medium size for peaches.

Vigor: Moderate at 4th year of growth.

Figure (form): Upright and spreading with open vase system of training. Productivity is very good for tree in fourth year of growth. Regularity of bearing appears to be regular (i.e., every year, not in alternate years).

Trunk size:

*Medium (diameter 9",10" above soil level).*—Moderately rough.

*Color.*—Grey 31 (15-C-6).

*Lenticels.*—Oval form, medium, and from 4–7 mm (0.16–0.28 inch) in length. Color — Light Brown (7-A-10). Number — many.

Branches:

*Size.*—Medium.

*Surface texture.*—Slightly rough. a. Mature — Slightly Rough b. Immature — Smooth Color Code (one year or older), Chestnut Brownstone (7-E-10). Color Code (immature), Calliste Green (19-L-6).

Three to four scaffold with lateral branches, at this stage of growth, being develop fruit wood and allow maximum sunlight for fruit colors. Diameter of scaffold branches taken at about two feet above soil level is five to six inches in circumference.

LEAVES

Size: Medium to large.

Length: 155 mm–165mm (6.10–6.50 inch).

Width: 38 mm–41 mm (1.50–1.61 inch). Shape: Lanceolate, leaf tip acuminate. Texture: Smooth. Color code:

*Upwardly disposed surface (upper side).*—Mt. Vernon Green (23-J-8).

*Downwardly disposed surface (underside).*—Near Mignard Green (21-I-6).

Marginal form: Crenate.

Leaf vein:

*Color code.*—Piquant green (20-K-6).

*Thickness.*—1½ mm (0.06 inch).

Glandular characteristics: Reniform — alternate.

*Color.*—Crysolite green (19-K-3).

*Size.*—2 mm.

*Number.*—Two.

Petiole:

*Size.*—Medium.

*Length.*—10–11 mm (0.37–0.43 inch).

*Diameter.*—2 mm (0.08 inch).

*Color code.*—Piquant green (20-K-6).

FLOWERS

Flower buds: Hardy under typical central San Joaquin Valley climate condition.

*Size.*—Dormant buds of average size.

*Length.*—10.13 mm (0.406 inch).

*Form.*—Conic and slightly appressed to the bearing wood.

Bud scales:

*Color.*—Rosetone (6-C-9) and very pubescent on surface.

Generally: Showy type.

Date of bloom: 5–10% as of Feb. 24, 2000, 100% bloom on Mar. 8, 2000, comparable to date of parent 'Island King', pp #9,199.

Size: Generally medium to large.

Diameter: When fully expanded – 32 mm (1.26 inch) to 40 mm (1.51 inch).

Bloom quality: Abundant.

No fragrance:

Petals:

*Size.*—Medium to large. Length — 15 mm (0.59 inch) to 18 mm (0.71 inch). Width — 12 mm (0.47 inch) to 15 mm (0.59 inch).

*Form.*—Broadly ovate.

*Number.*—Five.

*Color.*—From light pink (1-C-3) to (1-E-2) with older petals.

*Petal claws.*—Broadly truncate. Width — 1 mm (0.254 inch). Length — 1.5 mm (0.59 inch).

*Petal margins.*—Moderately undulated with somewhat rounded margins.

*Flower pedicel.*—Very short 2–3 mm (0.079 inch–0.12 inch). Color — Calliste Green (19-L-6). Surface — glabros. Diameter — 1–2 mm.

Sepals:

*Surface.*—Pubescent.

*Size.*—Medium to large.

*Form.*—Broadly ovate.

*Color.*—Maroon (7-H-4).

*Number.*—Five.

Calyx: Color Green (18-K-7) at base and Maroon (7-H-4) near base of sepals.

Anthers:

*Size.*—Average.

*Color.*—50 — red near dianthe. On dorsal side and edges +10F4. (Pale chamois) on ventral side.

Stamen: 10–12 mm (0.039–0.47 inch).

*Number.*—18–24.

Filament: Color very light pink (1-D-1).

Pistil:

*Length.*—Average 18 mm.

*Number.*—One.

*Color.*—Reed Green (19-D-2).

*Surface.*—Pubescent.

FRUIT

Date of maturity: May 8–10 in a normal year.

Size:

*Diameter axial plane.*—73–83 mm (2.87–3.27 inch with 64% of the larger size).

*Transverse in suture plane.*—62–67 mm (2.44–2.67 inches).

*Transverse at rt. angle to suture plane.*—71–77 mm (2.80–3.03 inches).

Form: Uniform.

*Symmetrical or asymmetrical.*—Shape of fruit is slightly asymmetrical.

Suture: Shallow but with distinct Pinard Yellow (9-J-2) coloration from base to apex.

Ventral surface: Uneven.

Stem cavity:

*Width.*—14–15 mm (0.55–0.59 inch).

*Depth.*—9–10 mm (0.35–0.39 inch).

*Length.*—16–18 mm (0.63–0.71 inch).

*Shape.*—Oval.

Stem: Short.

*Diameter.*—4–8 mm (0.16–0.2 inch).

Apex: Slightly Rounded.

Pistil point: Oblique.

Skin: Thickness normal for peach, slightly pubescent.

Texture: Firm.

Tendency: None observed.

Color code:

*Blush color.*—Peony, Burmese Ruby (7-H-6).

*Ground color.*—Varies over 50% at axis, Sunset (10-C-4).

*Flesh color.*—Jonquil (9-J-5).
*Color at surface of pit cavity.*—Jonquil (9-J-5).
*Color of pit well.*—Jonquil (9-J-5).
Juice production: Moderate.
Flavor: Very good to excellent.
Aroma: Good.
Texture: Firm.
Fibers:
*Number.*—Few.
*Texture.*—Firm.
Ripening: Even.
Eating quality: Very good to excellent.
Stone:
*Attachment.*—Clingstone.
*Fibers.*—Numerous, Short, SI. Thick.
*Size.*—Medium. Length — 35–40 mm (1.38–1.5 inch). Width — 26–28 mm (1.02–1.1 inch). Diameter — 18–20 mm (0.71 –0.74 inch).
Form: Ovate.
Apex: Sharply acute.
Color code, when dry: Near Toast (38-E-8).
Base: Slightly rounded.
Sides: Unequal.
Texture: Pitted.
Ridges: On both sides of stone with ventral edge relatively narrow.
Tendency to split: Only one in six fruit had split pits. None evident externally.
Use: Fresh market.
Shipping and quality: Very good.

Like most peach trees, the new variety has winter hardiness, and is not susceptible to damage during the dormant season. The fruit and foliage of the new variety do not evidence any particular susceptibilty to heat.

The above description of this new variety of peach tree is based on the growing conditions prevailing near Kingsburg, Calif. in the Central San Joaquin Valley of California, variations of the usual magnitude and characteristics may occur due to change in cultural factors, including irrigation, fertilization, primary climatic changes, et al.

What is claimed is:

1. A new and distinct variety of peach tree as described and illustrated which is somewhat similar to 'Island King' U.S. Plant Pat. No. 9,199, from which is a bud sport but from which it is distinguished by producing fruit that ripens ten to fourteen days after 'Island King' with good exterior coloration and very good eating quality which are mature for commercial harvesting and shipment approximately May 8 to 10 in a normal year.

* * * * *

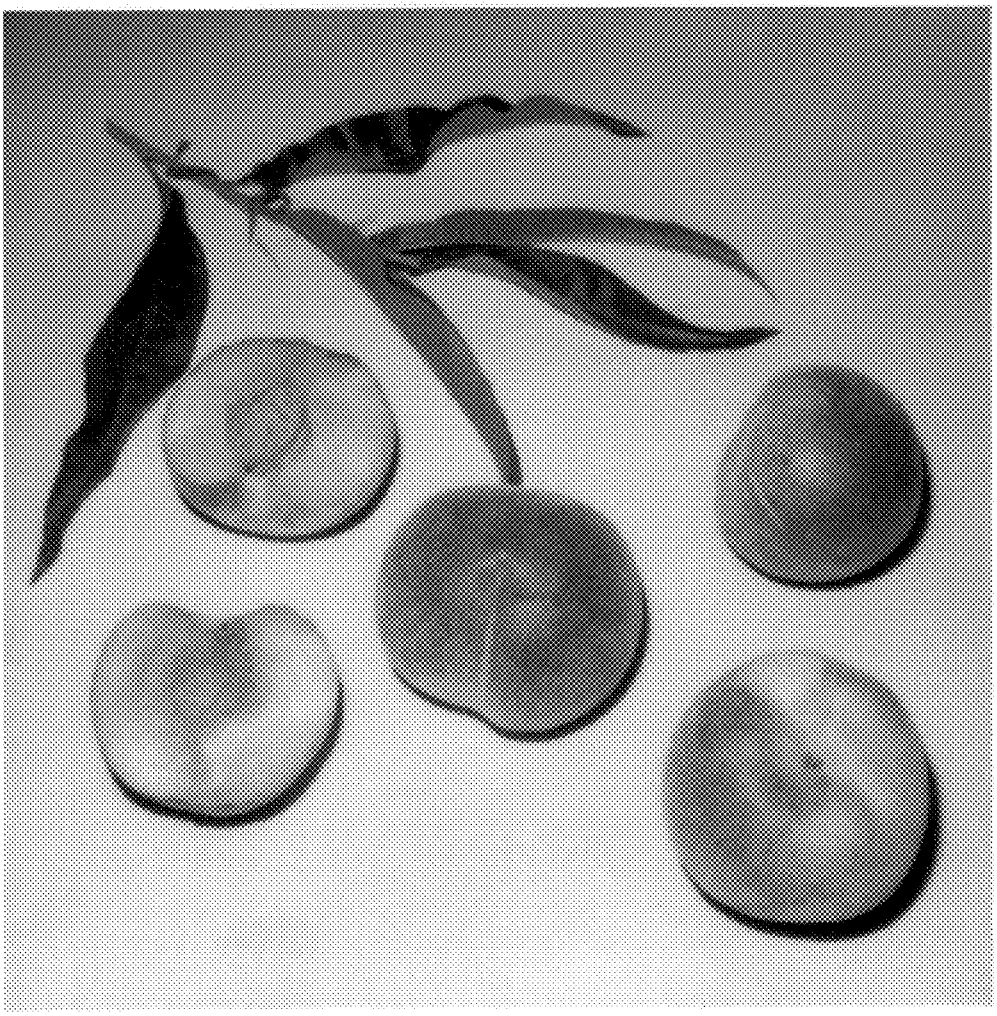

UNITED STATES PATENT AND TRADEMARK OFFICE

CERTIFICATE OF CORRECTION

PATENT NO. : PP 12,102 P2
APPLICATION NO. : 09/580400
DATED : September 25, 2001
INVENTOR(S) : Alan R. Asdoorian and Lora A. Asdoorian It is certified that error appears in the above-identified patent and that said Letters Patent is hereby corrected as shown below:

Column 1:

| | |
|---|---|
| Line 23: | Replace “ORGIN” with --ORIGIN-- |
| Line 32: | Replace “orgin” with --origin-- |

Column 2:

| | |
|---|---|
| Line 4: | Insert --it-- between “which” and “is distinguishable” |
| Line 29: | Replace “or” with --of-- |

Column 3:

| | |
|---|---|
| Line 4: | Replace “diameter 9”,10” above” with --diameter 9” at 10” above-- |
| Line 18: | Replace “scaffold” with --scaffolds-- |
| Line 19: | Delete “being” |
| Line 39: | Insert --(.08 inch)-- after “2mm” |
| Line 62: | Replace “pp#” with --Plant Patent No.-- |

Column 4:

| | |
|---|---|
| Line 9: | Replace “0.254” with --0.039-- |
| Line 10: | Replace “0.59 inch” with --0.059 inch-- |
| Line 26: | Replace “50 - red near dianthe” with --Red Near Dianthus (5-K-3)-- |
| Line 27: | Replace “(Pale chamois)” with --Chamois (11-I-5)-- |
| Line 28: | Replace “0.039” with --0.39-- |
| Line 32: | Insert --(.72 inch)-- after “18 mm” |
| Line 58: | Replace “4-8 mm” with --4-5 mm-- |

Column 5:

| | |
|---|---|
| Line 15: | Replace “SI” with --slightly-- |

UNITED STATES PATENT AND TRADEMARK OFFICE

CERTIFICATE OF CORRECTION

PATENT NO. : PP 12,102 P2
APPLICATION NO. : 09/580400
DATED : September 25, 2001
INVENTOR(S) : Alan R. Asdoorian and Lora A. Asdoorian It is certified that error appears in the above-identified patent and that said Letters Patent is hereby corrected as shown below:

Column 6:

| | |
|---|---|
| Line 17: | Replace "as" with --is-- |
| Line 19: | Insert --it-- between "which" and "is a bud" |
| Line 22: | Insert --and-- between "quality" and "which" |

Signed and Sealed this

Twenty-ninth Day of December, 2009

David J. Kappos

David J. Kappos
*Director of the United States Patent and Trademark Office*